July 26, 1949. F. H. HOWARD Plant Pat. 855
ROSE PLANT
Filed May 14, 1947
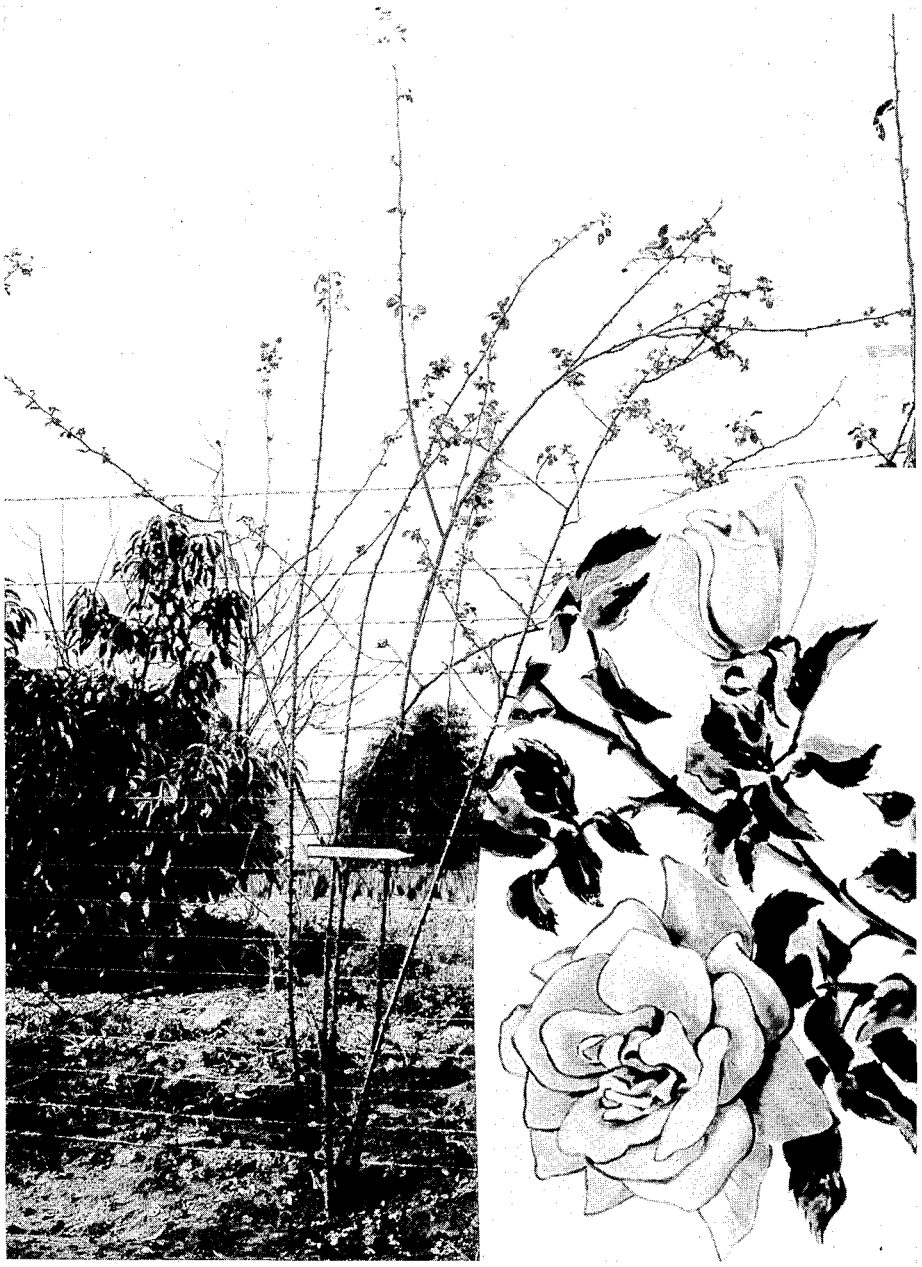
HEIGHT OF FENCE 8 FEET
HEIGHT OF PLANT APPROXIMATELY 12 FEET
INVENTOR
Frederick Huber Howard
By Orville M. Kile
Plant Patent Agt.

Patented July 26, 1949

Plant Pat. 855

UNITED STATES PATENT OFFICE

855

ROSE PLANT

Frederick Huber Howard, Montebello, Calif., assignor to Howard & Smith, Montebello, Calif.

Application May 14, 1947, Serial No. 748,027

1 Claim. (Cl. 47—61)

My present discovery relates to a new and distinct variety of climbing hybrid tea rose plant, it being substantially like the bush form of the Douglas MacArthur (Plant Patent 581), from which it sported, except that it has the climbing quality, its foliage is slightly larger, and its blooms are considerably larger.

This new variety is a prolific producer of large flowers of good form and color and is a very strong grower, being particularly resistant to mildew. It is a persistent and continuous bloomer from early spring to late fall. The unusual color of the flower makes it a welcome addition to the list of climbing hybrid teas.

The accompanying illustration shows a photographic reproduction of a plant of this variety growing in my garden. The inset on the right is of the flower, bud and foliage of this variety.

The following description is much the same as that found in Plant Patent No. 581, since much of the new plant is identical with the parent.

*The plant*

Growth: Vigorous, climbing, upright.

Health and disease resistance: Unusually resistant to mildew and other common diseases of roses. Does not die back.

Blooming habit: Continuous bloomer from early spring to late fall. Blooms borne singly on a stem, sometimes in clusters of three stems with the central bloom opening considerably in advance of the two lateral buds.

Stems: Very strong, heavy and stiff. New wood Yellowish Olive (Pl. XXX) and older wood Dull Citrine (Pl. XVI), both with reddish tinge usually showing on the side next to sun.

Thorns: A moderate number of thorns are found on the stems and these are large, flat, sharp, downward-pointing and reddish in color.

Foliage: Abundant in quantity, with three to seven leaflets which are round to elliptical with sharp apex, rounded base and finely serrated edge. Medium in size, 15 to 20 percent larger than in the bush form. Dark green on upper surface and lighter green with occasional red tinge on under surface. Upper surface smooth and glossy. Texture leathery.

*The flower*

Bud: Before expanding, the bud is long and pointed with thick base. The first color evident is Rose to Rose Red (Ridgway's, Pl. XII), with a touch of dark orange at the base. Ridgway's Standards include no color which would adequately describe the bud, but the color might be called "delft rose" or "oriental red" with bronze at the base. As the bud expands, the petals seem to take on a blend of the rose and bronze colors.

Blossom:

*Form.*—The same loose upright arrangement of petals found in the flower of the parent plant prevails, allowing the petals to stand apart distinctly. This makes an exquisite high form with full center which most of the specimens retain.

*Size.*—Large, measuring 4½ to 5½ inches in diameter when fully open.

*Petalage.*—From 24 to 30 petals, varying with the seasons.

*Color.*—Like the bud, the color of the flower is not found in Ridgway's Standards. A typical blossom is approximately the following color: rose to pink on outer several rows, with inside petals having a coral tinge, making the latter something like Grenadine Pink (Pl. II) or Strawberry Pink (Pl. I). Each petal has a small bronzy or yellow aiglet. As the flower ages it becomes more nearly Rose Color (Pl. XII).

*Fragrance.*—Moderate and very pleasing.

*Longevity.*—Excellent.

*Petals.*—Outer petals are nearly round and are deeply cupped, with smooth edges which sometimes curve but seldom curl.

Reproductive organs: *Pistils* are many, tightly bunched, partly enclosed in calyx, rising above the stamens. *Stamens* are many, surrounding the pistils. *Filaments* are of uneven lengths and shorter than the pistils; are light yellow with a red tinge at the base. *Anthers* are large and light yellow.

Having thus disclosed my discovery, I claim:

The new and distinct variety of hybrid tea rose plant herein disclosed, substantially like the Douglas MacArthur (Plant Patent No. 581), except that it is characterized particularly by its climbing ability, its slightly larger foliage, and its considerably larger buds and flowers.

FREDERICK HUBER HOWARD.

No references cited.